United States Patent
Deisenroth et al.

(10) Patent No.: US 10,092,500 B2
(45) Date of Patent: *Oct. 9, 2018

(54) ORAL CARE COMPOSITIONS

(71) Applicant: BASF SE, Ludwigshafen (DE)

(72) Inventors: Ted Deisenroth, Brookfield, CT (US); Glen Thomas Cunkle, Stamford, CT (US); Lauren Junker, Somerville, NJ (US); Michael Kuepfert, White Plains, NY (US); Paul Odorisio, Leonia, NJ (US); Steven N. Saunders, White Plains, NY (US); Vishal Ramnarine, Clifton, NJ (US); Neethu Abraham, New Rochelle, NY (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/302,873

(22) PCT Filed: Apr. 7, 2015

(86) PCT No.: PCT/US2015/024681
§ 371 (c)(1),
(2) Date: Oct. 7, 2016

(87) PCT Pub. No.: WO2015/157261
PCT Pub. Date: Oct. 15, 2015

(65) Prior Publication Data
US 2017/0216191 A1    Aug. 3, 2017

Related U.S. Application Data

(60) Provisional application No. 61/977,713, filed on Apr. 10, 2014, provisional application No. 61/977,721, filed on Apr. 10, 2014.

(51) Int. Cl.
| A61Q 11/00 | (2006.01) |
|---|---|
| A61K 8/72 | (2006.01) |
| A61K 8/362 | (2006.01) |
| A61K 8/44 | (2006.01) |
| A61K 8/88 | (2006.01) |
| A61K 8/49 | (2006.01) |
| A61K 8/46 | (2006.01) |
| A61K 8/27 | (2006.01) |
| A61K 8/21 | (2006.01) |
| C08G 69/44 | (2006.01) |

(52) U.S. Cl.
CPC .......... *A61K 8/88* (2013.01); *A61K 8/21* (2013.01); *A61K 8/27* (2013.01); *A61K 8/463* (2013.01); *A61K 8/4926* (2013.01); *A61Q 11/00* (2013.01); *C08G 69/44* (2013.01)

(58) Field of Classification Search
None
See application file for complete search history.

(56) References Cited

U.S. PATENT DOCUMENTS

| 2003/0152524 | A1 | 8/2003 | Eshita | |
| 2006/0052577 | A1* | 3/2006 | Swift | C08G 63/668 528/328 |
| 2006/0177416 | A1* | 8/2006 | Turnell | A61K 9/1075 424/78.27 |
| 2007/0020201 | A1* | 1/2007 | Boyd | A61K 8/27 424/52 |
| 2011/0008277 | A1 | 1/2011 | Bruggeman et al. | |
| 2011/0213036 | A1 | 9/2011 | Park et al. | |
| 2013/0095045 | A1 | 4/2013 | Groves et al. | |
| 2014/0027669 | A1 | 1/2014 | Detering et al. | |

FOREIGN PATENT DOCUMENTS

| EP | 2666517 A1 | 11/2013 |
| WO | 2007061794 A2 | 5/2007 |
| WO | 2008069622 A1 | 6/2008 |
| WO | 2009099455 A1 | 8/2009 |
| WO | 2013072932 A2 | 5/2013 |

OTHER PUBLICATIONS

PCT, International Preliminary Report on Patentability and Written Opinion of the International Searching Authority for PCT/US2015/024656, dated Jul. 27, 2015, 9 pages.
PCT, International Preliminary Report on Patentability and Written Opinion of the International Searching Authority for PCT/US2015/024681, dated Jun. 29, 2015, 8 pages.
Richard T. Tran et al., "Recent Developments on Citric Acid Derived Biodegradable Elastomers", Recent Patents on Biomedical Engineering, Nov. 2009, vol. 2, 12 pages.
Joost P. Bruggeman et al., "Biodegradable Xylitol-Based Polymers", 2008 WILEY-VCH Verlag GmbH & Co. KGaA, Weinheim, Apr. 21, 2008, 6 pages.
Andréa Gonçalves Antonio, "Caries preventive effects of xylitol-based candies and lozenges: a systematic review", Journal of Public Health Dentistry 71 (2011) pp. 117-124, American Association of Public Health Dentistry.
Extended European Search Report for PCT/US2015/024656, dated Apr. 8, 2017, 9 pages.

* cited by examiner

*Primary Examiner* — Brian Gulledge
(74) *Attorney, Agent, or Firm* — Lowenstein Sandler LLP

(57) ABSTRACT

The application relates to oral care compositions comprising substantive polyesteramides formed from polyols, polycarboxylic acids (or esters, anhydrides or halides thereof) and arginine. The formed polyesteramides are active in biofilm inhibition, biofilm dissolution and retarding or preventing acid production from oral bacteria.

15 Claims, No Drawings

ORAL CARE COMPOSITIONS

CROSS-REFERENCE TO RELATED APPLICATIONS

This application is a U.S. national stage of international application number PCT/US2015/024681, filed Apr. 7, 2015,which claims benefit of U.S. provisional application numbers 61/977,721 and 61/977,713, both filed on Apr. 10, 2014, each of which are incorporated herein by reference in their entireties.

FIELD OF INVENTION

The application relates to oral care compositions comprising substantive polyesteramides formed from polyols, polycarboxylic acids (or esters, anhydrides or halides thereof) and arginine. The formed polyesteramides are active in biofilm inhibition and biofilm dissolution.

BACKGROUND

Dental plaque is present to some degree in the form of a film on dental surfaces. It is a byproduct of microbial growth, and comprises a dense microbial layer consisting of a mass of microorganisms embedded in a polysaccharide matrix. It is reported that plaque adheres firmly to dental surfaces and is removed only with difficulty even through a rigorous brushing regimen. Moreover, plaque rapidly re-forms on the tooth surface after it is removed. Plaque may form on any part of the tooth surface, and is found particularly at the gingival margin, in cracks in the enamel, and on the surface of dental calculus. The problem associated with the formation of plaque on the teeth lies in the tendency of plaque to build up and eventually produce gingivitis, periodontitis and other types of periodontal disease, as well as dental caries, bad breath (halitosis) and dental calculus.

As plaque is formed by oral bacteria, a wide variety of antibacterial agents have been proposed to retard plaque formation and the oral infections associated with plaque formation. For example, halogenated hydroxydiphenyl ether compounds such as triclosan are well known to the art for their antibacterial activity and have been used in oral compositions to counter plaque formation by bacterial accumulation in the oral cavity.

Xylitol is also well known to inhibit the growth of *Streptococcus mutans* an oral bacteria implicated in plaque formation, and that this inhibition causes reduced acid formation which in turn is believed to inhibit caries formation. In the case of xylitol, because of its high water solubility the compound is quickly removed from the oral site, thus having a limited inhibitory effect upon reduced acid formation from *S. mutans*.

These antibacterial agents which work to reduce plaque formation by temporary reduction in the population of oral bacteria have numerous disadvantages when incorporated into commercial products, including disadvantages stemming from regulatory frameworks of various jurisdictions, compatibility with mouth rinse formulation, staining effects on tooth surface, and substantivity to oral surfaces.

Accordingly, there remains a need in the art for new oral compositions that reduce or prevent plaque formation whilst overcoming the above disadvantages.

SUMMARY OF THE INVENTION

The above objectives are achieved via oral care compositions comprising polymers formed from the reaction of polyols with polybasic carboxylic acids, anhydrides, esters or acid halides thereof and arginine.

Accordingly this application envisions a number of oral care compositions comprising these terpolymers.

The formed terpolymers are characterized by biofilm inhibition, biofilm disruption, inhibition of bacterial acid production and substantivity to oral tissues and tooth surfaces.

Thus the present application is directed to oral care composition comprising
  polymers formed from a polyol;
  polycarboxylic acids, anhydrides, esters or acid halides compounds, and
  arginine;
  wherein the formed polymer is distributed in an orally acceptable carrier.

More specifically this application is directed to oral care composition comprising the polymer of formula (I)

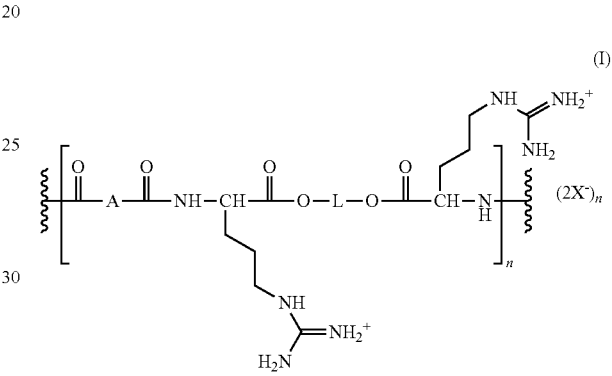

L is branched or unbranched $C_1$-$C_{20}$ alkylene, a branched or unbranched $C_2$-$C_{20}$ alkylene interrupted by one or more oxygens, $C_3$-$C_{12}$ cycloaliphatic, a monosaccharide radical, oligosaccharide radical or a polyether, which branched or unbranched $C_1$-$C_{20}$ alkylene, $C_2$-$C_{20}$ or $C_2$-$C_{12}$ cycloaliphatic may be substituted or unsubstituted by OH;

A is a linear or branched unsubstituted $C_1$-$C_{20}$ alkylene or a linear or branched $C_1$-$C_{20}$ alkylene substituted by $C(O)OR^1$, $C(O)O^-$ or OH;

A is a linear or branched unsubstituted $C_2$-$C_{20}$ alkylene interrupted by one or more —O— or $NR^2$— or a linear or branched $C_1$-$C_{20}$ alkylene substituted by $C(O)OR^1$, $C(O)O^-$ or OH;

wherein $R^1$ is hydrogen, unsubstituted linear or branched $C_1$-$C_{20}$ alkylene, linear or branched
  $C_1$-$C_{20}$ substituted by $C(O)OR^1$, $C(O)O^-$ or OH and
$R^2$ is hydrogen or linear or branched $C_1$-$C_{20}$ alkylene substituted by C(O)OH or OH;

X is any organic or inorganic orally acceptable anion.

Normally the number of positive charges on the polyguanidiniums will equal the negative charges for $X^-$;

and n is an integer ranging from 2 to 5000, preferably 2 or 3 to 3000;

wherein the formed polymer is distributed in an orally acceptable carrier.

In another embodiment, this application encompasses a number of methods:

Inhibiting bacterial plaque in the oral cavity by contacting the oral epithelial tissues and/or teeth of a mammal with a composition comprising polymers according to formula (I) above distributed in an orally acceptable carrier.

Retarding or preventing the acid production from oral bacteria comprising the step of contacting the oral epithelia tissues and/or teeth of a mammal with an oral care composition comprising the polymer of formula (I) above distributed in an orally acceptable carrier.

Disrupting a biofilm in an oral cavity by contacting the oral epithelial tissues and/or teeth of a mammal with an oral care composition comprising the polymer of formula (I) above distributed in an orally acceptable carrier.

Reducing dental sensitivity comprising applying to a surface of a mammalian tooth an oral care composition comprising
- a polymer formed from the condensation of
- a polyol;
- and
- a polycarboxylic acid, anhydride, ester or acid halide thereof;
- and
- arginine and the formed polymer is distributed in an orally acceptable carrier.

Sweetening or thickening an oral care composition by adding a polymer thereto formed from
the condensation of
- a polyol;
- and
- a polycarboxylic acid, anhydride, ester or acid halide thereof;
- and
- arginine to an oral care composition
and the polyol is selected from group consisting of sorbitol, xylitol, maltitol, erythritol, lactitol, isomalt and mannitol.

It is also believed that the xylitol arginine di esters and salts thereof are novel. Thus the intermediates are claimed per se:

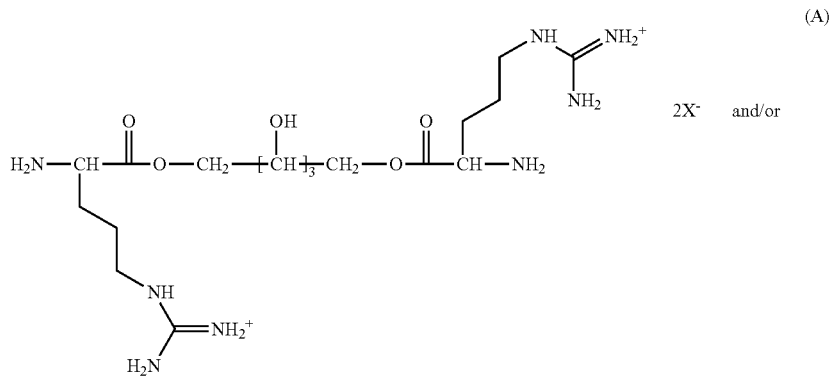

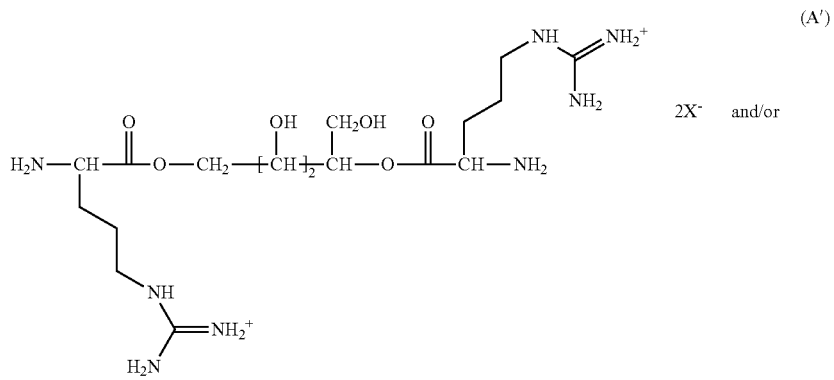

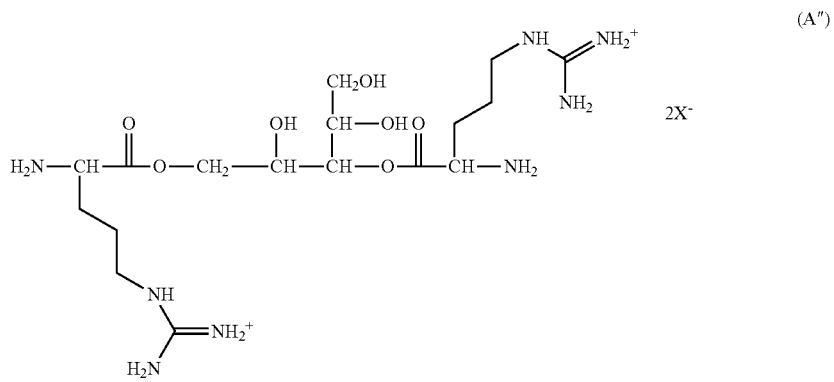

Also envisioned is the use of the formed terpolymer above:
To inhibit bacterial plaque in the oral cavity,
To disrupt biofilm and/or retard acid production from oral bacterial in an oral cavity,
To slowly release arginine to the oral cavity
To reduce dental sensitivity
To sweeten or thicken an oral care composition provided the polyol is selected from group consisting of sorbitol, xylitol, maltitol, erythritol, lactitol, isomalt and mannitol.

Further envisioned is a method of sweetening or thickening an oral care composition by adding a polymer formed from the condensation of
a polyol;
and
a polycarboxylic acid, anhydride, ester or acid halide thereof;
and
arginine to an oral care composition
and the polyol is selected from group consisting of sorbitol, xylitol, maltitol, erythritol, lactitol, isomalt and mannitol.

DETAILED DESCRIPTION OF THE INVENTION

Oral Care

As used herein, the term "oral care" refers to both therapeutic and prophylactic treatment of diseases and disorders affecting the oral cavity or associated medical conditions. Oral diseases and disorders include, but are not limited to: plaque, dental caries; periodontal diseases (e.g., gingivitis, adult periodontitis, early-onset periodontitis, etc.); mucosal infections (e.g., oral candidiasis, herpes simplex virus infections, recurrent aphthous ulcers, etc.); oral and pharyngeal cancers; and precancerous lesions.

Orally Acceptable Carrier

The term "orally acceptable carrier" includes any conventional oral delivery system, such as dental care products, food products and chewing gum. Examples of dental care product may include but are not limited to, films (i.e. whitening strips, dissolvable mouth wash strips), dentifrices, topical solutions or pastes, mouthwashes in the form of liquids or sprays or slurries, powders, gels or tablets and dental flosses. Examples of food products which may contain oral compositions described herein include, but are not limited to, lozenges, chewing gums and confections.

Molecular Weight

When the term molecular weight is used this will normally indicate a weight average molecular weight ($M_w$) unless otherwise indicated.

Comprising

Comprising for purposes of the invention is open ended, that is other components may be included. Comprising is synonymous with containing or including.

Condensants

Condensants for purposes of this application means molecules which come together to eliminate water, alcohol or a conjugate acid such as HCL and form a polymer. Normally the condensants are for example multifunctional alcohols, amines, acids, acid halides, esters or anhydrides. A $C_1$-$C_{20}$ glycol will condense with an alkyl diacid to form a polyester while a diamine will condense with a diacid to form a polyamide. The applicants include anhydrides as possible condensants although water is already eliminated when the anhydride is formed. An acid halide or acid chloride will condense with polyols to eliminate for example HCL.

Terpolymer

Terpolymer for purposes of this application means a polymer formed from 3 or more monomers, or condensants for example a polyol, diacid and arginine.

Biofilm

As used herein, the term "biofilm" refers to the film formed from the attachment of microorganisms to surfaces and the subsequent development of multiple layers of cells.

Dental Plaque

As used herein, the term "dental plaque" refers to the diverse microbial community (predominantly bacteria) found on the tooth surface, embedded in a matrix of polymers of bacterial and salivary origin. Plaque is used synonymously with biofilm.

Inhibition

As used herein, the term "inhibition" refers to at least a decrease of dental plaque-associated bacterial growth and/or biofilm formation.

Arginine Terpolymers

The arginine ter polymers formed from a polyol, polycarboxylic acids, anhydrides, esters or acid halides compounds, and arginine.

Polyols

Suitable examples of alcohols or polyols, which may be employed in the polymerization process are not especially limited except the polyols must be at least dihydric polyols. Thus the term "polyols" include polyols having an average OH functionality of at least 2 such as branched and unbranched aliphatic and cycloaliphatic alcohols, polyether alcohols, sugar alcohols, monosaccharides and oligosaccharides.

More specifically, the polyols may be selected from the group of linear or branched aliphatic alcohols having OH functionality of at least 2 for example the group consisting of ethylene glycol, 1,2-propanediol, 1,3-propanediol, 1,3-butanediol, 1,4-butanediol, 1,6-hexanediol, diethylene glycol, 1,4-cyclohexanediol, 1,4-cyclohexanedimethanol, neopentyl glycol, glycerol, trimethylolpropane, pentaerythritol, sorbitol, mannitol, glucose, fructose, inositol, xylitol, sorbitol, sucrose, threitol, erythritol, adonitol(ribitol), arabitol (lyxitol), dulcitol(galactitol), maltitol and isomalt, arabinose, ribose, xylose, mannose, galactose and glucose, maltose, maltotriose, maltotetraose, saccharose, lactose, leucrose, isomaltulose, chitobiose, chitotriose and chitotetraose, polyethyleneoxide and polypropyleneoxide.

The at least dihydric polyols may for example conform to formula (II)

$$HO\text{-}L\text{-}OH \qquad (II)$$

wherein L is branched or unbranched $C_1$-$C_{20}$ alkylene, $C_3$-$C_{12}$ cycloaliphatic, a sugar alcohol, a monosaccharide, oligosaccharide or a polyether, which branched or unbranched $C_2$-$C_{20}$ alkylene may be interrupted or uninterrupted by one or more nonconsecutive oxygens and/or substituted or unsubstituted by one or more OH, which $C_3$-$C_{12}$ cycloaliphatic may be substituted or unsubstituted by OH.

$C_1$-$C_{20}$ alkylene means for example linear or branched alkylene substituted or unsubstituted with OH, e.g., methylene, 1,2-ethylene, 1,2- or 1,3-propylene, 1,2-, 1,3- or 1,4-butylene, 1,1-dimethyl-1,2-ethylene or 1,2-dimethyl-1,2-ethylene, 1,5-pentylene, 1,6-hexylene, 1,8-octylene, 1,10-decylene, 1,12-dodecylene, 2-(hydroxymethyl)-2-ethylpropane, 2,2-dimethyl propane, and 2,2-bis(hydroxymethyl) propane.

Branched or unbranched $C_1$-$C_{20}$ alkylene interrupted by one or more nonconsecutive oxygens will for example be a $C_2$-$C_{20}$ alkylene for example —$CH_2$—O—$CH_2$—, —$CH_2CH_2$—O—$CH_2CH_2$—, —$CH_2CH_2CH_2$—O—$CH_2$—$CH_2$—$CH_2$—, —$CH_2(CH_3)CH_2CH_2$—O—$CH_2$— and —$CH_2CH_2$—O—$CH_2CH_2$—O—$CH_2CH_2$—.

$C_3$-$C_{12}$ cycloaliphatic means for example cyclopropyl, cyclobutyl, cyclopentyl, trimethylcyclohexyl or cyclohexyl.

The sugar alcohols may for example be selected from sorbitol, mannitol, inositol, xylitol, threitol, erythritol, adonitol(ribitol), arabitol(lyxitol), dulcitol(galactitol), maltitol and isomalt, preferably xylitol, sorbitol and mannitol (sweeteners).

Monosaccharides are for example arabinose, ribose, xylose, mannose, galactose and glucose.

Oligosaccharides contain from 2 up to 4 monosaccharide units and are for example maltose, maltotriose, maltotetraose, saccharose, lactose, leucrose, isomaltulose, chitobiose, chitotriose and chitotetraose.

The polyethers are for example polyalkylene oxides such as polyethyleneoxide and polypropyleneoxide.

Polycarboxylic Acids, Anhydrides, Esters or Acid Halides Thereof Compounds

Polycarboxylic acids, anhydrides, esters or acid halides thereof means for purposes of this application two or more carboxylic acids or derivatives of the two or more carboxylic acids. By derivatives it is meant that the carboxylic acid groups may be $C_1$-$C_4$ alkyl esters, free acids, anhydrides or acid halides. This would include compounds such as dicarboxylic acids, tricarboxylic acids and tetracarboxylic acids esters, anhydrides, dianhydrides or acid halides thereof.

The terms "polycarboxylic acids, anhydrides, esters or acid halides compounds" can be represented by the formula (III). These compounds are used in the preparation of polymers of formula (I) above.

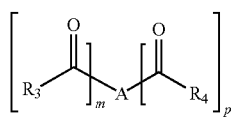

(III)

A is a linear or branched unsubstituted $C_1$-$C_{20}$ alkylene or a linear or branched $C_1$-$C_{20}$ alkylene substituted by C(O)OR$^1$, C(O)O$^-$ or OH, or A is a linear or branched unsubstituted $C_2$-$C_{20}$ alkylene interrupted by —O— or NR$^2$— or a linear or branched $C_2$-$C_{20}$ alkylene interrupted by —O— or NR$^2$ substituted by C(O)OR$^1$, C(O)O$^-$ or OH;

wherein R$^1$ is hydrogen, unsubstituted linear or branched $C_1$-$C_{20}$ alkylene, linear or branched $C_1$-$C_{20}$ alkylene substituted by C(O)OH, C(O)O$^-$ or OH and R$^2$ is hydrogen or linear or branched $C_1$-$C_{20}$ alkylene substituted by C(O)OH or OH;

m and p are 1 or 2;
and

R$^3$ and R$^4$ are independently OH, halogen, OR$^5$, —CO(O) which —CO(O) is bound to A to form a cyclic anhydride or R$^3$ is oxygen and R$^4$ is a bond to R$^3$, R$^5$ is a $C_1$-$C_4$ alkyl or a substituted or unsubstituted phenyl.

It is preferable that A is a linear or branched unsubstituted $C_1$-$C_{10}$ or a linear or branched $C_1$-$C_{10}$ alkylene substituted by C(O)OR1, C(O)O$^-$ or OH,
or A is a linear or branched unsubstituted $C_2$-$C_{10}$ alkylene interrupted by NR$^2$ or a linear or branched $C_2$-$C_{10}$ alkylene interrupted by NR$^2$ substituted by C(O)OR$^1$, C(O)O$^-$ or OH and R$^2$ is hydrogen or linear or branched $C_1$-$C_{10}$ alkylene substituted by C(O)OH or OH.

Most preferably A is a linear or branched unsubstituted $C_{1-10}$ alkylene or a linear or branched $C_1$-$C_8$ alkylene substituted by C(O)OR1, C(O)O$^-$ and OH
or A is a linear or branched $C_2$-$C_8$ interrupted by NR$^2$ and R$^2$ is $C_{1-8}$ alkylene substituted by C(O)OH.

$C_1$-$C_{20}$ alkylene includes $C_1$-$C_{10}$ alkylene, $C_1$-$C_8$ alkylene and $C_1$-$C_6$ alkylene.

Examples of $C_1$-$C_{20}$ alkylene dicarboxylic acids, $C_1$-$C_{20}$ alkylene tricarboxylic acids and $C_1$-$C_{20}$ alkylene tetracarboxylic acids or esters thereof are for example malonic acid, succinic acid, glutaric acid, adipic acid, pimelic acid, suberic acid, sebacic acid, azelaic acid, citric acid, diglycolic acid, 1,2,3-propanetricarboxylic acid, 1,1,3,3-propanetetracarboxylic acid, 1,1,2,2-ethane tetracarboxylic acid, 1,2,3,4-butanetetracarboxylic acid, 1,2,2,3 propanetetracarboxylic acid, 1,3,3,5 pentanetetracarboxylic acid, $C_1$-$C_4$ alkyl esters thereof, acid halides thereof, anhydrides thereof such as ethylenediaminetetraacetic dianhydride and combinations thereof.

Branched or unbranched unsubstituted $C_1$-$C_{20}$ alkylene interrupted by —O— or NR$^2$— or a linear or branched $C_1$-$C_{20}$ alkylene interrupted by —O— or NR$^2$ substituted by C(O)OR$^1$, C(O) O$^-$ or OH are for example ethylenediamine tetraacetic acid, ethyleneglycolbis-tetraacetic acid, diglycolic acid, ethylenediamine tetrapropionic acid, iminodiacetic acid, 1,2-propylenediaminetetraacetic acid, N-methyl, -ethyl, -propyl and -butyl iminodiacetic acid, 1,3-propylenediaminetetraacetic acid, N-hydroxyethylethylenediaminetriacetic acid, triethylenetetraminehexaacetic acid and diethylenetriaminepentaacetic acid.

The $C_1$-$C_{20}$ alkylene di, tri or tetra carboxylic acids may be substituted by hydroxy. Examples of hydroxyl substituted $C_1$-$C_{20}$ alkylene dicarboxylic acids, tricarboxylic acids and tetracarboxylic acids are malic acid, tartronic acid, citric acid, isocitric acid, tartaric acid and mucic acid, $C_1$-$C_4$ alkyl esters thereof, acid halides thereof, anhydrides thereof and combinations thereof.

Especially important examples of anhydrides are succinic anhydride, glutaric anhydride, adipic anhydride, pimelic anhydride, acetyl citric anhydride, the anhydride of diglycolic acid, the mono and dianhydrides of propanetetracarboxylic acid, the mono or dianhydrides of butanecarboxylic acid and ethylenediaminetetraacetic dianhydride are of particular interest.

Thus the polycarboxylic acid, esters, anhydrides and halides may for example be selected from the group consisting of malonic acid, succinic acid, glutaric acid, adipic acid, pimelic acid, suberic acid, sebacic acid, azelaic acid, citric acid, diglycolic acid, 1,2,3-propanetricarboxylic acid, 1,1,3,3-propanetetracarboxylic acid, 1,1,2,2-ethane tetracarboxylic acid, 1,2,3,4-butantetetracarboxylic acid, 1,2,2,3 propanetetracarboxylic acid, 1,3,3,5 pentanetetracarboxylic acid, ethylenediaminetetraacetic dianhydride, malic acid, tartronic acid, isocitric acid, tartaric acid, mucic acid gluconic acid, ethylenediamine tetraacetic acid, ethyleneglycol-bis-tetraacetic acid, diglycolic acid, ethylenediamine tetrapropionic acid, iminodiacetic acid, 1,2-propylenediaminetetraacetic acid, N-methyl, -ethyl, -propyl and -butyl iminodiacetic acid, 1,3-propylenediaminetetraacetic acid, N-hydroxyethylethylenediaminetriacetic acid, triethylenetetraminehexaacetic acid and diethylenetriaminepentaacetic acid, $C_1$-$C_4$ alkyl esters, acid halides and anhydrides thereof.

A preferable listing of polycarboxylic acids, esters or anhydride is malonic acid, succinic acid, glutaric acid, adipic acid, citric acid, isocitric acid, tartaric acid, mucic acid, diglycolic acid, ethylenediaminetetraacetic acid or $C_1$-$C_4$ alkyl esters thereof, anhydrides (i.e. ethylenediaminetetraacetic dianhydride for example) thereof, acid halides thereof and combinations thereof.

Arginine

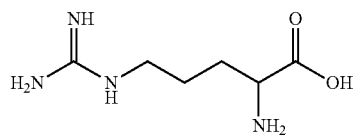

Arginine is an amino acid. When arginine is reacted with a polyol, the free acid arginine will effectively condense to form an ester bond. This intermediate can then be reacted with a polycarboxylic acid, anhydride, ester or acid halide thereof to form the terpolymer of formula (I) which may be dispersed in an orally acceptable carrier to give the oral composition of the application.

Thus the oral care composition will comprise the polymer of formula (I)

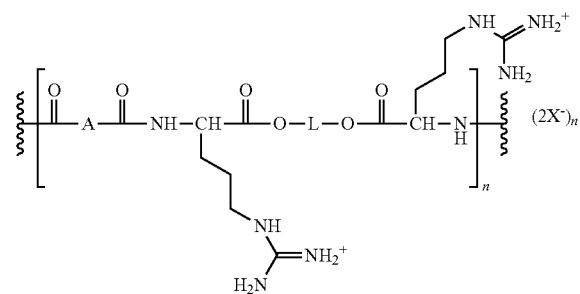

wherein,

L is branched or unbranched $C_1$-$C_{20}$ alkylene, a branched or unbranched $C_2$-$C_{20}$ alkylene interrupted by one or more oxygens, $C_3$-$C_{12}$ cycloaliphatic, a monosaccharide radical, oligosaccharide radical or a polyether, which branched or unbranched $C_1$-$C_{20}$ alkylene, branched or unbranched $C_2$-$C_{20}$ alkylene interrupted by one or more oxygens or $C_3$-$C_{12}$ cycloaliphatic may be substituted or unsubstituted by OH;

A is a linear or branched unsubstituted $C_1$-$C_{20}$ alkylene or a linear or branched $C_1$-$C_{20}$ alkylene substituted by C(O)OR$^1$, C(O)O$^-$ or OH;

A is a linear or branched unsubstituted $C_2$-$C_{20}$ alkylene interrupted by one or more —O— or NR$^2$— or a linear or branched $C_1$-$C_{20}$ alkylene substituted by C(O)OR$^1$, C(O)O$^-$ or OH;

wherein R$^1$ is hydrogen, unsubstituted linear or branched $C_1$-$C_{20}$ alkylene, linear or branched $C_1$-$C_{20}$ substituted by C(O)OR$^1$, C(O)O$^-$ or OH and R$^2$ is hydrogen or linear or branched $C_1$-$C_{20}$ alkylene substituted by C(O)OH or OH;

X is any organic or inorganic orally acceptable anion. For example X$^-$ may be phosphate, phosphonate, carbonate, bicarbonate, chloride, bisulfate, sulfate, formate, acetate, citrate, oxalate, tartrate, glycolate, gluconate, malate, ascorbate and ethylenediaminetetraacetic acid and envisioned.

Normally the number of positive charges on the polyguanidiniums will equal the negative charges for X$^-$;

and n is an integer ranging from 2 to 5000, preferably 2 or 3 to 3000;

wherein the formed polymer is distributed in an orally acceptable carrier.

Arginine for example may be condensed with xylitol to form a xylitol ester of arginine. This xylitol ester of arginine can then be reacted with a polycarboxylic acid, ester or anhydride to form a polyesteramide terpolymer of any one or a combination of formulae (IV, IV', IV").

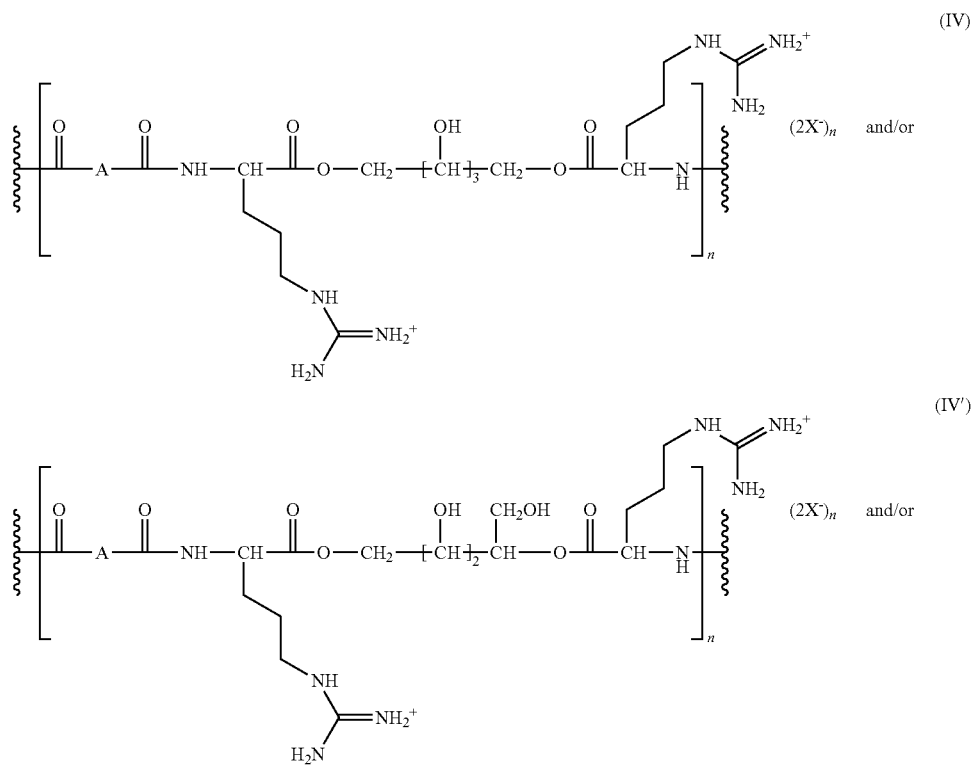

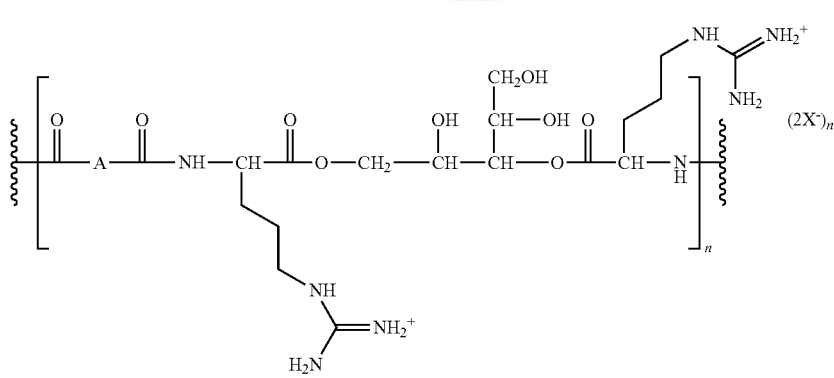

(IV″)

A is a linear or branched unsubstituted $C_1$-$C_{20}$ alkylene or a linear or branched $C_1$-$C_{20}$ alkylene substituted by C(O)OR$^1$, C(O)O$^-$ or OH;
or
A is a linear or branched unsubstituted $C_2$-$C_{20}$ alkylene interrupted by —O— or NR$^2$— or a linear or branched $C_2$-$C_{20}$ alkylene interrupted by NR$^2$ and substituted by C(O)OR$^1$, C(O)O$^-$ or OH;
wherein R$^1$ is hydrogen, unsubstituted linear or branched $C_1$-$C_{20}$ alkylene, linear or branched $C_1$-$C_{20}$ substituted by C(O)OR$^1$, C(O)O$^-$ or OH and R$^2$ is hydrogen or linear or branched $C_1$-$C_{20}$ alkylene substituted by C(O)OH or OH;
X is any organic or inorganic orally acceptable anion.

For example X$^-$ may be phosphate, phosphonate, carbonate, bicarbonate, chloride, bisulfate, sulfate, formate, acetate, citrate, oxalate, tartrate, glycolate, gluconate, malate, ascorbate and ethylenediaminetetraacetic acid is envisioned.

Normally the number of positive charges on the polyguanidiniums will equal the negative charges for X$^-$; and n is an integer ranging from 1, 2 or 3 to 5,000. Preferably n is 3 to 3,000.

It is preferable that A is a linear or branched unsubstituted $C_1$-$C_{10}$ or a linear or branched $C_1$-$C_{10}$ alkylene substituted by C(O)OR1, C(O)O$^-$ or OH,
or
A is a linear or branched unsubstituted $C_2$-$C_{10}$ alkylene interrupted by NR$^2$ or a linear or branched $C_2$-$C_{10}$ alkylene interrupted by NR$^2$ substituted by C(O)OR$^1$, C(O)O$^-$ or OH, R$^2$ is hydrogen or linear or branched $C_1$-$C_{10}$ alkylene substituted by C(O)OH or OH. Most preferably A is a linear or branched unsubstituted $C_1$-$C_8$ alkylene or a linear or branched $C_1$-$C_8$ alkylene substituted by C(O)OR1, C(O)O$^-$ and OH
or
A is a linear or branched $C_1$-$C_8$ interrupted by NR$^2$ and R$^2$ is $C_1$-$C_8$ alkylene substituted by C(O)OH.

To name a few of the possible terpolymers encompassed by the present application:
Polyester amides of xylitol, arginine and succinic acid terpolymers;
Polyester amides of xylitol, arginine and ethylenediaminetetraacetic acid (or dianhydride thereof) terpolymers
Polyester amides of xylitol, arginine and citric acid terpolymers;
Polyester amides of ethylene glycol, arginine and ethylenediaminetetraacetic acid (or dianhydride thereof) terpolymers
Polyester amides of mannitol, arginine and citric acid terpolymers;
Polyester amides of sorbitol, arginine and ethylenediaminetetraacetic acid (or dianhydride thereof) terpolymers;
Polyester amides of pentaerythritol, arginine and citric acid terpolymers;
The formed polymer of formula (I or IV) will vary in Mw from 500 to about 1,000,000, preferably from about 1000 to about 800,000, most preferably about 1500 to about 500,000.

The oral care composition according to the application containing polymers of formula (I) will contain about 3 to about 90 or 95 wt. % arginine, preferably about 5% to about 76 wt % of the total weight of the formed polymer.

The oral care composition will comprise about 0.01 to about 75 wt. %, preferably about 0.1 to about 50 wt. %, most preferably about 0.2 to about 10 or 20 wt. % of the formed arginine containing polymer based on the total weight of the oral care composition.

The concentration of the arginine terpolymer may be quite high in a lozenge, gum or candy. For example the terpolymer may make up about 0.01% to 95 wt. % of the candy, gum or lozenge.

This application as explained above includes not only oral care compositions but various methods and uses.

In particular:

A method for inhibiting bacterial plaque in the oral cavity by contacting the oral epithelial tissues and/or teeth of a mammal with an oral care composition comprising the polymer formed from polyols, polycarboxylic acids, anhydrides, esters or acid halides compounds, and arginine or alternatively polymers of formula (I) and the formed polymer or polymer of formula (I) is distributed in an orally acceptable carrier.

A method of retarding or preventing acid production from oral bacteria comprising the step of contacting the oral epithelia tissues and/or teeth of a mammal with an oral care composition comprising a polymer formed from, polyols, polycarboxylic acids, anhydrides, esters or acid halides compounds, and arginine or alternatively polymers of formula (I) and the formed polymer or polymers of formula (I) is distributed in an orally acceptable carrier.

A method of disrupting a biofilm in an oral cavity by contacting the oral epithelial tissues and/or teeth of a mammal with a composition comprising a polymer formed from polyols, polycarboxylic acids, anhydrides, esters or acid halides compounds, and arginine or alternatively polymers of formula (I), and the formed polymer or polymers of formula (I) is distributed in an orally acceptable carrier is envisioned.

A method of reducing dental sensitivity comprising applying to the teeth of a mammal a composition comprising a polymer formed from polyols, polycarboxylic acids, anhydrides, esters or acid halides compounds, and arginine or alternatively polymers of formula (I), and the formed polymer or polymers of formula (I) is distributed in an orally acceptable carrier is envisioned.

A method of sweetening or thickening an oral care composition by adding a polymer formed from the condensation of a polyol; and a polycarboxylic acid, anhydride, ester or acid halide thereof; and arginine or alternatively polymers of formula (I) to an oral care composition and the polyol is selected from group consisting of sorbitol, xylitol, maltitol, erythritol, lactitol, isomalt and mannitol.

The oral care composition of this application may of course contain a number of other ingredients. For example in addition to the arginine containing polymers of the application the oral care composition may contain ingredients such as excipients, flavoring agents, antimicrobial agents, anti-caries agents, dentifrice vehicles, desensitizing agents, surfactants, anti-tartar agents, thickening agents, Excipients In some embodiments, an oral care composition in accordance with the present invention includes at least one excipient. Excipients suitable for use in the present invention include any compound that is conventionally used in oral care compositions.

Suitable excipients for an oral composition in accordance with the present invention may be chosen from: preservatives, abrasives (smoothing agents), further antibacterial agents, inflammation-inhibiting agents, irritation-preventing agents, irritation-inhibiting agents, further antimicrobial agents, antioxidants, binders, (mineral) fillers, buffers, carrier materials, chelating agents (chelate formers), cleaning agents, care agents, surface-active substances, emulsifiers, enzymes, foam-forming agents, foam stabilizers, foam boosters, gelling agents, gel-forming agents, bleaching agents, smell- and/or taste-modulating agents, smell- and/or taste-reducing agents, smell- and/or taste-enhancing agents, plasticizers, (mucous membrane)/skin cooling agents (cooling substances), (mucous membrane)/skin soothing agents (mucous membrane)/skin cleansing agents, (mucous membrane)/skin care agents, (mucous membrane)/skin healing agents, mucous membrane-protecting agents, stabilizers, suspending agents, vitamins, colorants, color-protecting agents, pigments, surfactants, electrolytes, silicone derivatives, polyols, calcium carbonate, calcium hydrogen phosphate, aluminum oxide, fluorides, zinc, tin, potassium, sodium and strontium salts, pyrophosphates, hydroxyapatites.

In some embodiments, an oral care composition in accordance with the present invention includes at least one excipient, wherein the at least one excipient is chosen from: surfactants, desensitizing agents, whitening agents, tartar control agents, antibacterial agents, abrasives, chelants including silica, binders and thickening agents, detergents, adhesion agents, foam modulators, pH modifying agents, mouth-feel agents, sweeteners, flavoring agents, colorants, preservatives, combinations thereof, and the like.

Flavoring Agents

In some embodiments, an oral care composition in accordance with the present invention includes a flavoring agent. In some embodiments, the flavoring agent is a member chosen from: mucous membrane cooling agents, mucous membrane warming agents, sharp-tasting substances, sweeteners, sugar substitutes, organic or inorganic acidifiers (e.g., malic acid, acetic acid, citric acid, tartaric acid, phosphoric acid), bitter principles (e.g., quinine, caffeine, limonine, amarogentine, humolones, lupolones, catechols, tannins), edible mineral salts (e.g., sodium chloride, potassium chloride, magnesium chloride and sodium phosphates), essential oils (e.g., oils of spearmint, peppermint, wintergreen, *sassafras*, clove, sage, *eucalyptus*, marjoram, cinnamon, lemon, lime, grapefruit, and orange), menthol, carvone, anethole, and combinations thereof.

Abrasives

Abrasives suitable for use in the present invention include silica materials and particularly silica gels and precipitated amorphous silica having an oil absorption value of less than 100 cc/100 g silica and preferably in the range of from 45 cc/100 g to less than 70 cc/100 g silica. Oil absorption values are measured using the ASTM Rub-Out Method D281. Low oil absorption silica abrasives particularly useful in the practice of the present invention are marketed under the trade designation Sylodent® XWA (Davison Chemical Division of W. R. Grace & Co., Baltimore, Md. 21203). Sylodent® 650 XWA, a silica hydrogel composed of particles of colloidal silica having a water content of 29% by weight averaging from 7 to 10 microns in diameter, and an oil absorption of less than 70 cc/100 g of silica is a preferred example of a low oil absorption silica abrasive useful in the practice of the present invention. Another low oil absorption silica abrasive particularly useful in the practice of the present invention is marketed under the trade designation DP-105™ (J. M. Huber Chemicals Division, Havre de Grace, Md. 21078) is a precipitated amorphous silica having an average particle size distribution from 5 to 12 microns and an oil absorption in the range of 50 to 70 cc/100 g. Other abrasives which may be used in the practice of the present invention include precipitated silicas having a mean particle size of up to 20 microns, such as Zeodent® 115, (J. M. Huber Chemicals Division, Havre de Grace, Md. 21078), or Sylodent® 783 (Davison Chemical Division of W. R. Grace & Company), sodium metaphosphate, potassium metaphosphate, tricalcium phosphate, dihydrated dicalcium phosphate, aluminum silicate, calcined alumina, bentonite or other siliceous materials, or combinations thereof.

In some embodiments, an oral care composition in accordance with the present invention includes an abrasive excipient. In some embodiments, the abrasive excipient is a silica material. In some embodiments, the silica material is colloidal particles having an average particle size ranging from 3 microns to 12 microns. In some embodiments, the colloidal particles have an average particle size ranging from 5 to 10 microns and a pH range from 4 to 10 preferably 6 to 9 when measured as a 5 wt. % slurry. In some embodiments, the silica material is a low oil absorption silica abrasive. In some embodiments, the low oil absorption silica abrasive is present in the oral care compositions of the present invention at a concentration of 5 wt. % to 40 wt. %. In some embodiments, the low oil absorption silica abrasive is present at a concentration of 10 wt. % to 30 wt. %.

In some embodiments, the abrasive excipient is a member chosen from: silicic acids, calcium carbonates, calcium phosphates, aluminum oxides and/or hydroxyapatites, sodium metaphosphate, potassium metaphosphate, tricalcium phosphate, dihydrated dicalcium phosphate, aluminum silicate, calcined alumina, bentonite, surface-active substances (e.g., sodium lauryl sulfate, sodium lauryl sarcosinate, and cocamidopropylbetaine), and other siliceous materials, and combinations thereof.

In some embodiments, the abrasive excipient may be used individually as the sole abrasive in preparing an oral care composition of the present invention or in combination with other known dentifrice abrasives. In some embodiments, the total quantity of abrasive excipient present in the dentifrice compositions of the present invention is 5 wt. % to 60 wt. %. In some embodiments, the abrasive excipient is present in an amount of 10 wt. % to 55 wt. % by weight when the dentifrice composition is a toothpaste.

Anti-Microbial Agents

Anti-microbial agents suitable for use in the present invention include nonionic antibacterial agents, including halogenated diphenyl ether compounds such as 2,4,4'-trichloro-2'-hydroxydiphenyl ether (Triclosan) and 2,2'-dihydroxy-5,5'-dibromodiphenyl ether. Other useful nonionic antibacterial agents include phenolic compounds including phenol and its homologs, mono and polyalkyl and aromatic halophenols, resorcinol and its derivatives and bisphenolic compounds, such phenolic compounds being more fully disclosed in U.S. Pat. No. 5,368,844, the disclosure of which is incorporated herein by reference.

In some embodiments, an oral care composition in accordance with the present invention includes an anti-microbial agent. In some embodiments, the anti-microbial agent is a member chosen from: triclosan, chlorhexidine and its salts (e.g., its acetate, gluconate or hydrochloride), peroxides, phenols and their salts, domiphen bromide (phenododecinium bromide), bromochlorophene, Zn salts, chlorophylls, Cu salts, Cu gluconate, Cu chlorophyll, sodium lauryl sulfate, polylysine, quarternary monoammonium salts such as cocoaliphaticbenzyldimethylammonium chloride or also pyridinium salts such as cetyl pyridinium chloride, stannous fluoride and combinations thereof.

Thymol, menthol, methyl salicylate and eucalyptol and mixtures thereof are well known as antimicrobials and active in the prevention of plaque and gingivitis.

In some embodiments, the anti-microbial agent is a nonionic antibacterial agent. In some embodiments, the nonionic antibacterial agent is included in a dentifrice composition at a concentration of 0.001 wt. % to 5 wt. %. In some embodiments, the nonionic antibacterial agent is present in an amount of 0.01 wt. % to 1.2 wt. %.

Anti-microbial agents of particular interest are quarternary monoammonium salts such as cocoaliphaticbenzyldimethylammonium chloride or also pyridinium salts such as cetyl pyridinium chloride, polylysine, thymol, menthol, methyl salicylate and eucalyptol, triclosan, chlorhexidine and its salts (e.g., its acetate, gluconate or hydrochloride) and combinations thereof.

The oral care composition will typically contain the polymer of formula (I) and chlorhexidine or polylysine. It has been discovered that these combination are synergistic.

Anti-Caries Agents

In some embodiments, an oral composition in accordance with the present invention includes an anti-caries agent. In some embodiments, the anti-caries agent is a fluoride ion source chosen from: inorganic fluoride salts, such as soluble alkali metal, alkaline earth metal salts (e.g., sodium fluoride, stannous fluoride, potassium fluoride, ammonium fluoride, calcium fluoride), a copper fluoride such as cuprous fluoride, zinc fluoride, barium fluoride, sodium fluorosilicate, ammonium fluorosilicate, sodium fluorozirconate, ammonium fluorozirconate, sodium monofluorophosphate, aluminum mono- and di-fluorophosphate, fluorinated sodium calcium pyrophosphate, and combinations thereof.

Dentifrice Vehicles

In some embodiments, an oral care composition in accordance with the present invention includes an orally-acceptable dentifrice vehicle. In some embodiments, the dentifrice vehicle includes a humectant therein. Humectants suitable for use in the present invention include glycerin, sorbitol, xylitol, and/or propylene glycol of molecular weight in the range of 200 to 1,000. As used herein, "sorbitol" refers to the material typically commercially available as a 70% aqueous solution. In some embodiments, the humectant concentration is from 5 wt. % to 70 wt. % of the oral composition.

In some embodiments, an oral care composition in accordance with the present invention includes water. Water employed in the preparation of commercially suitable toothpastes should preferably be deionized and free of organic impurities. In some embodiments, water is present in an amount of 15 wt. % to 30 wt. % of the oral composition. In some embodiments, water is present in an amount of 10 wt. %. In some embodiments, these amounts of water include the free water which is added in addition to that which is introduced with other materials such as with sorbitol.

Surfactants

Surfactants suitable for use in the compositions of the present invention include any material able to achieve increased prophylactic action and render the oral care compositions more cosmetically acceptable. The surfactant is preferably a detersive material that imparts to the oral care composition detersive and foaming properties.

In some embodiments, an oral care composition in accordance with the present invention includes a surfactant. In some embodiments, an oral care composition in accordance with the present invention surfactant including higher alkyl sulfates such as sodium lauryl sulfate, sodium laureth sulfate, N-alkyl amides of glutamates such as sodium cocoyl glutamate, esters of ethoxylated fatty alcohol and citric acid such as laureth-7 citrate, and mono- and/or dialkyl sulfosuccinates such as sodium laureth sulfosuccinate.

In some embodiments, the surfactant is an enzyme-compatible surfactants chosen from: nonionic polyoxyethylene surfactants such as Poloxamer 407 and 335. These poloxamers are triblock copolymers composed of a central hydrophobic chain of polyoxypropylene(poly(propylene oxide)) flanked by two hydrophilic chains of polyoxyethylene (poly (ethylene oxide)). A further nonionic surfactant of interest is polyethylene glycol ethers of long chain fatty acids such as stearic acid for example Steareth 3.

Polysorbate 20 is a polyoxyethylene derivative of sorbitan monolaurate, which is distinguished from the other members in the polysorbate range by the length of the polyoxyethylene chain and the fatty acid ester moiety and is useful in oral care compositions.

Polyalkyl glucosides are also of interest. They are derived from sugars and fatty alcohols. Examples or polyalkyl glucosides are lauryl glucoside, decyl glucoside, caprylyl/caproyl glucoside and coco glucoside to name a few.

Amphoteric surfactants such as cocamidopropyl betaine and cocamidopropyl betaine lauryl glucoside are also of interest. In some embodiments, an oral composition in accordance with the present invention includes a surfactant or a combination of surfactants at a total surfactant concentration in the dentifrice composition of 2 wt. % to 10 wt. %.

In some embodiments, the surfactant or combination of surfactants is present in an amount of 3.5 wt. % to 6.5 wt % by weight.

Anti-Tartar Agents

In some embodiments, an oral care composition in accordance with the present invention includes an anti-tartar agent. In some embodiments, the anti-tartar agent is chosen from: pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, sodium tripolyphosphate; long chain polyphosphates such as sodium hexametaphosphate; and cyclic phosphates such as sodium trimetaphosphate. In some embodiments, an anti-tartar agent is present in a dentifrice composition of the present invention at a concentration of 1 wt. % to 5 wt. %.

Desensitizing Agents

In some embodiments, the oral care composition may further contain desensitizing agents. For Example nitrate salt, a bicarbonate salt, potassium nitrate, arginine-bicarbonate-phytate complex, potassium citrate or oxalate and arginine may be added to the oral composition in combination with the presently disclosed terpolymers.

Thickening Agents

In some embodiments, an oral care composition in accordance with the present invention includes a thickening agent. In some embodiments, the thickener is selected from the group consisting of, but not limited to: calcium carbonate, titanium dioxide, silicon dioxide, talcum, aluminium oxide, dicalcium phosphate, tricalcium phosphate, magnesium hydroxide, cellulose thickeners such as carboxymethyl cellulose, hydroxyalkyl celluloses such as hydroxypropyl cellulose hydroxyethyl cellulose, gums such as xanthan gum, polyglycols and polyethylene glycol, inorganic thickeners (e.g., amorphous silica compounds, natural and synthetic clays, lithium magnesium silicate and magnesium aluminum silicate), and combinations thereof.

In some embodiments, the thickening agent is an organic thickener chosen from: natural and synthetic gums and colloids including cellulose thickeners such as carboxymethyl cellulose; hydroxyalkyl celluloses such as hydroxypropyl cellulose hydroxyethyl cellulose; gums such as xanthan gum; polyglycols of varying molecular weights; and polyethylene glycol. In some embodiments, the thickening agent is an inorganic thickener chosen from: amorphous silica compounds such as colloidal silicas compounds available under the trade designation Cab-o-Sil® (manufactured by Cabot Corporation and distributed by Lenape Chemical, Bound Brook, N.J.); Zeodent® 165 (J.M. Huber Chemicals Division, Havre de Grace, Md. 21078); Sylodent® 15 (Davison Chemical Division of W.R. Grace Corporation, Baltimore, Md. 21203); natural and synthetic clays; lithium magnesium silicate (Laponite); and magnesium aluminum silicate (Veegum). In some embodiments, the thickening agent is present in a dentifrice composition of the present invention in amounts of 0.1 wt. % to 10 wt. %. In some embodiments, the thickening agent is present in an amount of 0.5 wt. % to 4.0 wt. %.

Anti-Oxidants

In some embodiments, an oral composition in accordance with the present invention includes an anti-oxidant. In some embodiments, the anti-oxidant is chosen from: naturally occurring tocopherols and their derivatives (e.g., Vitamin E acetate), Vitamin C and its salts and derivatives (e.g., ascorbyl palmitate, Mg ascorbyl phosphate, ascorbyl acetate), Vitamin A and derivatives (Vitamin A palmitate), tocotrienols, flavonoids, alpha-hydroxy acids (e.g., citric acid, lactic acid, malic acid, tartaric acid) and their Na, Ka and Ca salts, flavonoids, quercetin, phenolic benzylamines, propyl gallate, octyl gallate, dodecyl gallate, butylhydroxyanisole (BHA, E320), butylhydroxytoluene (BHT, 2,6-di-tert.-butyl-4-methylphenol, E321), lecithins, mono- and diglycerides of edible fatty acids esterified with citric acid, carotenoids, carotenes (e.g., α-carotene, β-carotene, lycopene) and their derivatives, phytic acid, lactoferrin, EDTA, EGTA), folic acid and its derivatives, ubiquinone and ubiquinol and their derivatives, ferulic acid and its derivatives, zinc and its derivatives (e.g., ZnO, $ZnSO_4$), selenium and its derivatives (e.g., selenium methionine), orthophosphates and Na, K and Ca salts of mono-phosphoric acids, and constituents, extracts and fractions thereof isolated from plants, (e.g., tea, green tea, algae, grapeseeds, wheat germ, chamomile, rosemary, oregano), and combinations thereof.

Antioxidants of particular interest are octadecyl 3-(2,5-di-tert-butyl-4-hydroxyl phenyl propionate, tetrabutyl ethylidenebisphenol, and tetrakis (3-(3,5-di-tert-butyl-4-hydroxyphenyl)propionate.

Light stabilizers may also be included in the oral care composition. A good example of a benzotriazole is 2-(5-chloro-2H-benzotriazol-2-yl)-6-(1,1dimethylethyl)-4-methyl phenol.

Of particular interest are oral care composition comprising the arginine polymer described above wherein the oral care composition comprises at least one additional oral care ingredient selected from the group consisting of surfactants, desensitizing agents, chelating agents, whitening agents, tartar control agents, antibacterial agents, abrasives including silica, binders and thickening agents, detergents, adhesion agents, foam modulators, pH modifying agents, mouthfeel agents, sweeteners, flavoring agents, colorants, preservatives and combinations thereof.

The oral care composition comprising the arginine polymer described above will preferably be combined with an antibacterial agent selected from the group consisting of triclosan, stannous fluoride, chlorhexidine and its salts (e.g., its acetate, gluconate or hydrochloride), peroxides, phenols and their salts, domiphen bromide (phenododecinium bromide), bromochlorophene, Zn salts, chlorophylls, Cu salts, Cu gluconate, Cu chlorophyll, sodium lauryl sulfate, quarternary monoammonium salts such as cocoaliphaticbenzyldimethylammonium chloride or also pyridinium salts such as cetyl pyridinium chloride, polylysine, homopolymers of arginine and arginine salts or complexes and combinations thereof, preferably quarternary monoammonium salts such as cocoaliphaticbenzyldimethylammonium chloride or also pyridinium salts such as cetyl pyridinium chloride, polylysine, triclosan, chlorhexidine and its salts (e.g., its acetate, gluconate or hydrochloride) and combinations thereof.

Evaluation of Arginine Terpolymer Polymers

EXAMPLE 1

Experimental Procedure for the Preparation of Bis(p-Nitrophenyl) Succinate.

In a 1 L 3-neck flask, equipped with an overhead stirrer, addition funnel and thermometer, is dissolved 40.0 g (0.288 mole) of p-nitrophenol in 500 mL of acetone under a nitrogen atmosphere. To the resultant bright yellow solution is added 29.1 g (0.288 mole) of triethylamine. The resultant yellow solution is cooled to 5° C. and a solution of 21.2 g of succinoyl dichloride in 100 mL of acetone is added dropwise over a 1.5 hr period, an exotherm is noted during the addition. Upon completion of the addition the brown-red suspension is stirred at 5° C. for an additional hour and then allowed to warm to ambient temperature and stirred overnight. The resultant brown-purple suspension is added 1 g of succinoyl dichloride and stirred an additional 30 minutes at ambient temperature. Added 500 mL of deionized water and stirred at ambient temperature for 15 minutes. The product is isolated by filtration and the solid is washed with water and dried at 25 in Hg/55° C. in a vacuum oven to give 45 g brown-dark red powder. The product is purified by recrystallization from ethyl acetate to give 42 g of a bright brown powder.

EXAMPLE 2

Experimental Procedure for the Preparation of Bis(L-Arginine) Xylitol Diester

In a 2 L 4-neck flask, equipped with a Dean-stark trap, an overhead stirrer and thermometer, is added 17.4 g (0.1 mole) of L-arginine, 7.6 g (0.05 mole) of xylitol, 40 g (0.21 mole) of p-toluenesulfonic acid monohydrate and 1 L toluene under an argon atmosphere. The resultant mixture—is heated at 110° C. for 16 hr and 5.5 mL of water—is collected. Upon cooling the reaction mixture a yellow oil separated and the toluene layer—is decanted. The yellow oil is dissolved in isopropanol at 70° C., cooled to 4° C., and decanted isopropanol. The isopropanol treatment—is repeated 2 additional times. The product is dried on a rotary evaporator to give 50 g of a white powder.

EXAMPLE 3

Experimental Procedure for the Preparation of Arginine-Xylitol-Succinic Acid Polymer In a 50 ml round bottom flask is added 14 g (12.2 mmole) of tetra-p-toluenesulfonic acid salt of bis(L-arginine) xylitol diester, 4.4 g (12.2 mmole) bis(p-nitrophenyl) succinate and 14 g of dimethylsulfoxide under a nitrogen atmosphere. The mixture is mixed on a vortex mixer to form a brown solution and then heated at 75° C. To the resultant reaction mixture is added dropwise 2.7 g (26.8 mmole) of triethylamine. The resultant yellow solution is heated at 75° C. for 48 hr under nitrogen then cooled to ambient temperature. To the resultant reaction mixture is added 3 mL of ethyl acetate, stirred, and the supernatant decanted. Dissolved polymer in methanol, precipitated into ethyl acetate and decanted supernatant. The methanol/ethyl acetate precipitation procedure is repeated 2 additional times and the product is dried on a rotary evaporator to obtain 7.4 g of a yellow-brown powder. The polymer is purified by dialysis using a 3500 molecular weight cutoff membrane with a pH 7 buffer and freeze dried to obtain a white powder. A 10% aqueous solution of the polymer is prepared and the pH adjusted to 7.

EXAMPLE 4

Experimental Procedure for Preparation of Arginine-Xylitol-EDTA Polymer

In a 500 ml 3-neck flask, equipped with an overhead stirrer and thermocouple, is dissolved 5.75 g (5 mmole) of tetra-p-toluenesulfonic acid salt of bis(L-arginine) xylitol diester in 35 ml of anhydrous dimethylformamide under an argon atmosphere. To the resultant solution is added sequentially 1.28 grams (5 mmole) of ethylenediamine tetraacetic acid dianhydride, then 5 ml of anhydrous triethylamine. The resulting mixture is heated at 50° C. for 6 hr, then cooled to ambient temperature. Volatiles are removed under reduced pressure at 10 torr, 60° C. for 1 hr. The concentrated reaction mixture is dissolved into 100 ml of deionized water. The resultant solution is dialyzed (3500 molecular weight cutoff membranes) with deionized water and freeze dried to obtain 2.3 grams off-white powder. The polymer is dissolved into deionized water with addition of 2N sodium hydroxide solution to obtain a 10% solution of pH 7.

EXAMPLE 5

Experimental Procedure for Preparation of Arginine-Xylitol-Citric Acid Polymer

In a 250 ml 3-neck flask, equipped with an overhead stirrer, a nitrogen gas inlet and a distillation take-off, is dissolved 8.82 g (10 mmole) of dihydrochloride di-p-toluenesulfonic acid salt of bis(L-arginine) xylitol diester in 70 ml of anhydrous dimethylformamide under a nitrogen sweep. To the resultant solution is added 1.92 grams (10 mmole) of anhydrous citric acid. After the citric acid dissolved, 10 ml of anhydrous triethylamine is added, causing a white precipitate to separate from solution. The resulting mixture is heated at 130° C. with removal of distillate as it formed. After 6 hr the reaction mixture is a clear solution and is cooled to ambient temperature. Volatiles are removed under reduced pressure at 12 torr, 60° C. for 0.5 hr and then at 0.1 torr, 120° C. for 1 hr. The concentrated reaction mixture is dissolved into 250 ml of deionized water. A 140 ml portion of the resultant solution is dialyzed (3500 molecular weight cutoff membranes) with deionized water and freeze dried to obtain 0.43 grams beige powder. The polymer is dissolved into deionized water with addition of 2N sodium hydroxide solution to obtain a 10% solution of pH 7.

EXAMPLE 6

Experimental Procedure for Preparation of Arginine-Xylitol-Citric Acid Polymer (Random)

In a 250 ml 3-neck flask, equipped with an overhead stirrer, a nitrogen gas inlet and a distillation take-off, is heated a mixture of 1.52 grams (10 mmole) of xylitol, 2.11 grams (10 mmole) of L-arginine hydrochloride and 1.92 grams (10 mmole) of anhydrous citric acid at 130° C. under a nitrogen sweep. Water of reaction is removed as it formed. After 3 hr at 130° C. the reaction temperature is raised to 140° C. and the reaction mixture pressure is reduced to 50 torr for an additional 1.5 hr. The reaction melt is cooled under argon and dissolved into 50 ml of deionized water. The water solution is filtered (medium glass frit); then is dialyzed (3500 molecular weight cutoff membranes) with deionized water and freeze dried to obtain 1.28 grams off-white powder. The polymer is dissolved into deionized water with addition of 2N sodium hydroxide solution to obtain a 10% solution of pH 7.

APPLICATION EXAMPLES

Evaluation of Arginine Terpolymers

The terpolymers are evaluated using a number of different criteria:

Prevention of Biofilm Development

To evaluate the multispecies saliva and *S. mutans* biofilm preventing activity of polymers and control combinations of condensants For Multispecies Saliva Biofilms:

Hydroxy apatite (HA) coated surfaces of a 96 peg lid (Biosurface Technologies, Bozeman, Mont.) are pellicle treated with pooled human saliva 200 µl/per well of a 96 well clear plate for 30 minutes at 37° C. aerobically. Into each well of the growth plate, clear 96 well plate, 160 µl inoculated Brain Heart Infusion (BHI) broth is added. Test solutions are added to a desired final concentration and water is added to bring the final volume to 200 µl. The hydroxyl apatite coated pegs are added to the growth plate and incubated for 24 hr anaerobically at 37° C.

For *S. mutans* Biofilms:

*S. mutans* 25175 is inoculated into 10 mL BHI and incubated statically at 37° C. overnight. Then the culture is inoculated to OD 0.1 into Jordans 5% sucrose as the growth media. Hydroxy apatite coated peg lids are pellicle treated with sterile artificial saliva 200 µl/per well of a 96 well clear plate for 30 minutes at 37° C. aerobic. Into each well of the growth plate, clear 96 well plate, 160 µl inoculated Jordans 5% sucrose broth is added. Test solutions are added to a desired final concentration and water is added to bring the final volume to 200 µl. The pegs are added to the growth plate and incubated for 24 hr anaerobically at 37° C.

After 24 hr of growth time, pegs containing biofilms are transferred to a 96 well clear rinse plate containing 200 µl of sterile BHI or Sterile Jordans 5% sucrose for 5 minutes at room temperature. The pegs are then transferred to a white 96 well plate containing 200 µl of Bac-titer-Glo: this is incubated at room temperature for 10 minutes (shaking) and read for luminescence using a plate reader.

Substantitivity Compared to Xylitol Condensant Alone

Method to evaluate the substantivity of polymers to hydroxy apatite surfaces and the effects these polymers have on the growth of *Streptococcus mutans* and Saliva derived biofilms:

For Multispecies Saliva Biofilms:

Hydroxy apatite (HA) coated surfaces are pellicle treated with pooled human saliva 200 µl/per well of a 96 well clear plate for 30 minutes at 37° C. aerobically. Fresh human saliva is inoculated in Jordan's 5% sucrose at OD 0.17.

For *S. mutans* Biofilms:

*S. mutans* (ATCC#25175) is inoculated into 10 mL BHI and incubated statically at 37° C. overnight. Then the culture is inoculated to OD 0.21 into Jordans 5% sucrose as the growth media. Hydroxy apatite coated peg lids are pellicle treated with sterile artificial saliva 200 µl/per well of a 96 well clear plate for 30 minutes at 37° C. aerobically.

The peg lids are transferred to a clear 96 well plate containing 200 µl of the designated treatments below in Jordan's with 5% sucrose. This peg/plate assembly is shaken for 5 mins and then incubated for 25 mins aerobically at 37 C.

After 30 mins of treatment the two pegs is transferred to a 96 well plate containing 200 µl of water and it is rinsed for 10 min at 500 rpm. After 10 mins, the pegs are transferred to a plate containing 200 µl of the *S. mutans* culture or saliva and incubated for 24 hrs.

After incubation the peg lids are transferred to a rinse plate containing 200 µl of water for 5 minutes and then transferred to white 96 well plate containing 200 µl Bac-titer-Glo, this is shaken for 5 minutes and read for luminescence.

Method for Evaluating Disruption of Established Biofilms

Method to screen combinations of actives, example polymers and chelates to identify potential synergies for biofilm disruption:

Polystyrene pegs are pellicle treated with fresh pooled human saliva for 30 minutes at 37° C. aerobically. Saliva is inoculated into BHI broth at a final concentration of 10% saliva. 200 µl of inoculated or uninoculated media is added to each well. The pegs are added to the growth media and incubated anaerobically 37° C.

At 24 hr. the pegs are removed and transferred to a fresh plate containing 200 µl of sterile BHI. And incubated anaerobically for another 24 hr at 37° C.

After 48 hr of growth time, pegs containing the biofilms are transferred to a 96 well rinse plate containing 200 µl of BHI. Following a 5 minute rinse at room temperature, the pegs are transferred to a treatment plate containing combinations of actives, chelate and polymers. This is followed a 5 minute treatment (shaking at 500 rpm). The treated pegs are transferred to a white 96 well plate containing 200 µl Bac-titer-Glo reagent—this is incubated at room temperature for 5 minutes (shaking) and read on a plate reader for luminescence.

Inhibition of Bacterial Acid Production

Method to observe the acid production of *S. mutans* in a medium containing a pH indicator and glucose. Observe how xylitol and the example polymers affect acid production:

A culture of *S. mutans* (ATCC#25175) is grown statically overnight in 10 mL liquid broth (BHI) at 37° C. This culture is inoculated into fresh Bromo Cresol Purple (BCP) broth at 10%. 20 µl of 10% pH adjusted test solutions are added to each well of a clear 96 well plate. The no treatment control has 20 µl water added. To each experimental well 180 of the inoculated BCP broth is added. To the no inoculum control 20 µl water and 20 µl filter sterilized overnight culture broth are added.

The plate is shaken at 500 rpm for 5 minutes and then read for absorbance at both 588 nm (Absorption max at pH 6.8—purple) and 427 nm (Absorption max at pH 5.2—yellow). Both wavelengths are measured every hour for several hours but before evaporation became an issue. The plates are shaken for 10 seconds before reading.

Results

Prevention of Biofilm Formation:

Polymers are evaluated using the biofilm prevention method indicated above for both *S. mutans* and multispecies saliva derived biofilm.

The polymer examples performed as well as or better than the combinations of the condensant controls at similar concentrations. This observation is consistent for the prevention of both the *S. mutans* and saliva biofilms (See Table 1 and Table 2).

The composition of the xylitol, arginine and succinic acid polymer is 1:2:1 xylitol:arginine:succinic acid by moles and 25% xylitol, 56% arginine and 19% succinic acid by weight based on the total weight of the formed polymer.

The composition of the xylitol succinic acid polymer is 1:1 xylitol:succinic acid by moles and 56% xylitol and 44% succinic acid by weight.

TABLE 1

Prevention of *Streptococcus mutans* biofilm development.. Percentages are reported as reduction from the untreated control, negative values indicate an increase over the control.

| Material tested | Controls | Concentration of polymer or respective | | |
|---|---|---|---|---|
| | | 2.0% | 1.0% | 0.5% |
| Sterile control | 100% | | | |
| Untreated control | — | | | |
| 2% xylitol Control | −1% | | | |
| Arginine-Succinic acid-Xylitol polymer | | 63%[a] | 55%[b] | 41% |
| Arginine & Succinic acid & Xylitol control | | 77%[a] | 35% | −37% |

[a] comparison to 2% xylitol control. Student's t-test (p < 0.001)
[b] comparison to respective component control. Student's t-test (p < 0.001) (p < 0.001)

TABLE 2

Prevention of multispecies saliva biofilm development. Percentages are reported as reduction from the untreated control.

| Material tested | Controls | Concentration of polymer or respective control | | |
|---|---|---|---|---|
| | | 2.0% | 1.0% | 0.5% |
| Sterile control | 100% | | | |
| Untreated control | — | | | |
| 2% xylitol Control | 17% | | | |
| Arginine-Succinic acid-Xylitol polymer | | 92% [a] | 80% [a,b] | 56% [a] |
| Arginine & Succinic acid & Xylitol control | | 69% [a] | 59% [a] | 35% |

[a] comparison to 2% xylitol control. Student's t-test ($p < 0.001$)
[b] comparison to respective component control. Student's t-test ($p < 0.001$)

Substantitivity Compared to Xylitol Condensant Alone

Results: Polymers are evaluated using the Substantivity for biofilm prevention method indicated above for both *S. mutans* and multispecies saliva derived biofilms.

Cetyl pyridinium chloride at 0.7% is used as the positive control and it demonstrated retention of activity after rinsing in the model and is considered substantive.

Xylitol-succinic acid-arginine polymer shows substantivity when compared to individual components at comparable concentrations.

The observations are consistent for the prevention of both the *S. mutans* and saliva biofilms (See Table 3 and Table 4).

TABLE 3

Multispecies saliva derived Biofilm growth after 24 hr on pre-treated hydroxyapatite surfaces. Percentages are reported as reduction from the No Treatment control, negative values indicate an increase over the control.

| | % treatment | % decrease in biofilm as compared to growth control (negative indicates increased biofilm) |
|---|---|---|
| Growth Control | — | 100% |
| No treatment control | — | 0% |
| Cetylpyridinium chloride | 0.070% | 98% |
| Xylitol Control | 1.120% | 14% |
| | 2.000% | 12% |
| Arginine control | 1.120% | 49% |
| | 0.560% | −22% |
| | 0.280% | −24% |
| | 0.140% | −20% |
| | 0.070% | −28% |
| Xylitol-Arginine-Succinic acid polymer | 2.000% | 43% |
| | 1.000% | 45% |
| | 0.500% | 49% |
| | 0.250% | 54% |
| | 0.125% | 46% |

TABLE 4

*Streptococcus mutans* Biofilm Growth after 24 hr on Pre-treated Hydroxyapatite surfaces. Percentages are reported as reduction from the No Treatment control. Negative values indicate an increase over the control.

| | % treatment | % decrease in biofilm as compared to growth control (negative indicates increased biofilm) |
|---|---|---|
| Growth Control | — | 100% |
| No treatment control | — | 0% |
| Cetylpyridinium chloride | 0.070% | 100% |
| Xylitol Control | 1.120% | −11% |
| | 2.000% | −15% |
| Arginine control | 1.120% | −29% |
| | 0.560% | −53% |
| | 0.280% | −59% |
| | 0.140% | −18% |
| | 0.070% | −40% |
| Xylitol-Arginine-Succinic acid polymer | 2.000% | 37% |
| | 1.000% | 29% |
| | 0.500% | 27% |
| | 0.250% | 17% |
| | 0.125% | 0% |

Polymers are evaluated using the Biofilm disruption model as described above.

Example polymers (xylitol-arginine-succinic acid polymer) are combined with example actives (epsilon-polylysine and chlorhexidine) and a chelator (Ca EDTA).

Specific combinations gave significant improvement over the control combinations—see Table 5.

1000 ppm epsilon-Polylysine disrupted biofilm on its own. Combination of epsilon polylysine and 1% Arginine-xylitol-succinic acid polymer (with or without ca EDTA) give a significant benefit, see Table 5.

TABLE 5

Disruption of 48 hour saliva biofilms after treatment for 5 minutes. Percentages are reported as reduction from the No Treatment control, negative values indicate an increase over the control.

| | Sterility control | Active Chelate and Polymer | Active and Chelate control | Active and Polymer | Active control | Chelate and Polymer | Chelate control | Polymer | No treatment control |
|---|---|---|---|---|---|---|---|---|---|
| Active = 1000 ppm e-polylysine, Chelate = 0.1% Trilon Ca, Polymer = 1% | 100 [a,b,c] | 68 [a,b,c] | 31 [c] | 80 [a,b,c] | 29 [c] | −13 [b] | −10 | −7 [b] | 0 |

TABLE 5-continued

Disruption of 48 hour saliva biofilms after treatment for 5 minutes. Percentages are reported as reduction from the No Treatment control, negative values indicate an increase over the control.

| | Sterility control | Active Chelate and Polymer | Active and Chelate control | Active and Polymer | Active control | Chelate and Polymer | Chelate control | Polymer | No treatment control |
|---|---|---|---|---|---|---|---|---|---|
| Arginine-Xylitol-Succinic Acid Terpolymer | | | | | | | | | |

[a] comparison to no treatment control. Students t-test ($p < 0.001$)
[b] comparison to active control. Student's t-test ($p < 0.001$)
[c] comparison to polymer only control. Student's t-test ($p < 0.001$)

Inhibition of Bacterial Acid Production.

Controls: No inoculum control showed very little change as would be expected. The no treatment control showed a large change demonstrating acid production. Xylitol controls-minimally decreased Optical Density (OD) 588 in a dose response and also increase minimally at OD 427 indicating acid inhibition at all concentrations tested. L-Arginine controls gave similar results as the no treatment control-indicating no acid inhibiting effects. The citric acid, succinic acid and EDTA controls demonstrated no or little change demonstrating acid inhibiting effects.

In this experiment, little change in pH (or similar change to xylitol control) is observed with polymers: Arginine-Xylitol EDTA polymer, Arginine-Xylitol-Citric Acid polymer.

TABLE 6

Delta values at OD 588

| Treatment | Mean Delta OD588 (stdev) |
|---|---|
| No inoculum control | 0.15 (0.06) |
| No Treatment control | 1.063 (0.132) |
| 2% Xylitol | 0.734 (0.131) |
| 0.1% Xylitol | 0.993 (0.099) |
| 0.5% Xylitol | 0.841 (0.119) |
| 1% Xylitol | 0.759 (0.081) |
| 1% L-Arginine pH 6.3 | 1.054 (0.13) |
| 1% citric acid pH 7.0 | 0.196 (0.029) |
| 1% succinic acid pH 7.4 | 0.323 (0.107) |
| 1% EDTA pH 7.0 | 0.283 (0.086) |
| 1% Arginine-Xylitol EDTA polymer pH 6.5 | 0.423 (0.045) |
| 1% Arginine-Xylitol-Citric Acid polymer pH 6.4 | 0.569 (0.039) |
| 1% Arginine-Xylitol-Succinic Acid polymer pH 7 | 0.904 (0.038) |

Oral Care Formulations Containing the Arginine Terpolymers of the Invention Mouthwash

| Component | Parts by weight % |
|---|---|
| Glycerin | 7.5 |
| Polysorbate 80 | 0.12 |
| Ethanol | 15 |
| Sweetner combination (sorbitol, mannitol, xylitol) | 0.15 |
| Arginine terpolyer of the invention | 1-5 |
| Cetyl pyridinium chloride | 0.04 |
| Benzoic acid | 0.05 |
| Color | 0.05 |
| Peppermint flavor | 0.1 |
| Water | qs to 100 |

Mouthwash

| Component | Parts by weight % |
|---|---|
| Sorbitol | 10 |
| Glycerol | 10 |
| Ethanol | 15 |
| Propylene Glycol | 15 |
| Arginine terpolymer of the invention | 1-5 |
| Sodium lauryl sulfate | 0.5 |
| Sodium methylcocyl taurate | 0.25 |
| Polyoxypropylene/polyoxyethylene block copolymer | 0.25 |
| Peppermint flavor | 0.1 |
| Water | qs to 100 |

Peroxide Mouthwash

| Component | Parts by weight % |
|---|---|
| 35% $H_2O_2$ solution | 3.5-5% |
| Coolant (mint) | 0.07 |
| Flavor | 0.1-0.2 |
| Poloxamer 407 | 0.75 |
| Arginine terpolymer of the invention | 0.5-3 |
| Glycerin | 11.0 |
| Propylene glycol | 3.0 |
| Sweetener combination (sorbitol, mannitol) | 0.08 |
| Cetyl pyridinium chloride | 0.1 |
| Sodium citrate | 0.2 |
| Water | qs to 100 |

Toothpaste Formulation

| Component | Parts by weight % |
|---|---|
| Sodium bicarbonate | 40-45 |
| Tetra sodium pyrophosphate | 2.0 |
| NaF | 0.2 |
| Sorbitol | 35-40 |
| Arginine terpolymer of the invention | 1-5 |
| Polyethylene glycol | 1.0 |
| Sodium carboxymethylcellulose | 0.7 |
| Sodium saccharin | 1.0 |
| Flavor | 0.8-1 |
| Sodium lauryl sulfate | 0.3 |
| Sodium lauroyl sarcosinate | 1.0 |
| Water | qs to 100 |

Toothpaste Formulation

| Ingredient | Formula A | Formula B |
|---|---|---|
| SnF2, USP | 0.45 | 0.45 |
| Zinc citrate | 0.5 | 0.5 |
| Zinc Lactate | — | — |
| Sorbitol (LRS) USP | 45 | 45 |
| Fused Silica (TecoSil 44CSS) | — | 15 |
| Silica Z119 | 2.5 | 0 |
| Silica Z109 | 12.5 | 0 |
| Hydroxyethyl cellulose (HEC Natrasol 250M) | 0.5 | 0.5 |
| CMC 7M8SF | 1.3 | 1.3 |
| Carrageenan mixture | 0.7 | 0.7 |
| Sodium lauryl sulfate (48397-002) | 4 | 4 |
| Saccharin Sodium | 0.5 | 0.5 |
| Sodium Gluconate | 1 | 1 |
| Arginine terpolymer of the invention | 1-5 | 1-5 |
| Flavor | 1 | 1 |
| Water, USP | QS | QS |

Lozenge Formulation

| Component | Parts by weight % |
|---|---|
| Sugar | 75-98 |
| Corn syrup | 1-20 |
| Flavor oil | 0.1-1.0 |
| Tablet lubricant | 0.1-5 |
| Arginine terpolymer of the invention | 1-5 |
| Sodium salt of hydrolyzed methoxy ethylene-maleic anhydride copolymer (1:1 mw 70,000) | 0.05 |
| Water | .01-2 |

Lozenge Formulation

| Component | Parts by weight % |
|---|---|
| Sodium saccharin | 0.15 |
| Flavor | 0.25 |
| Magnesium Stearate lubricant | 0.40 |
| Color | 0.01 |
| Arginine terpolymer of the invention | 1-50 |
| PEG (40) Sorbitan diisostearate | 1 |
| Sodium salt of hydrolyzed methoxy ethylene-maleic anhydride copolymer (1:1 mw 70,000) | 0.30 |
| Sorbitol | qs to 100 |

Chewing Gum

| Component | Parts by weight % |
|---|---|
| Gum Base | 10-50 |
| Binder | 3-10 |
| Filler | 5-8 |
| Sorbitol, mannitol or combination | 0.1-5 |
| Arginine terpolymer of the invention | 1-5 |
| Flavor | 0.1-5 |

The invention claimed is:
1. An oral care composition comprising:
a polymer formed from the condensation of:
xylitol;
a polycarboxylic acid, anhydride, ester or acid halide thereof; and
arginine;
wherein the formed polymer is distributed in an orally acceptable carrier.
2. The oral care composition according to claim 1, wherein the polymer formed is defined by formula (I)

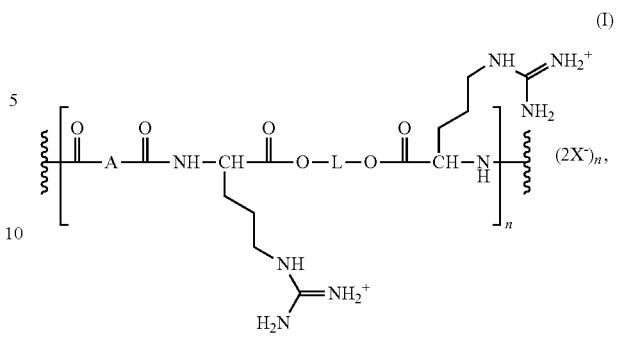

wherein L is a xylitol radical;
A is a linear or branched unsubstituted $C_1$-$C_{20}$ alkylene or a linear or branched $C_1$-$C_{20}$ alkylene substituted by —C(O)OR$^1$, —C(O)O$^-$ or —OH; A is a linear or branched unsubstituted $C_1$-$C_{20}$ alkylene interrupted by one or more —O— or —NR$^2$—; or a linear or branched $C_1$-$C_{20}$ alkylene substituted by —C(O)OR$^1$, —C(O)O$^-$ or —OH;
wherein R$^1$ is hydrogen, unsubstituted linear or branched $C_1$-$C_{20}$ alkylene, linear or branched $C_1$-$C_{20}$ substituted by —C(O)OR$^1$, —C(O)O$^-$ or —OH; and
R$^2$ is hydrogen or linear or branched $C_1$-$C_{20}$ alkylene substituted by —C(O)OH or —OH;
X is any organic or inorganic orally acceptable anion;
and n is an integer ranging from 2 to 5000;
wherein the formed polymer is distributed in an orally acceptable carrier.
3. The oral care composition according to claim 1, wherein the polycarboxylic acids, anhydrides, acid halides or esters thereof are defined by formula (III)

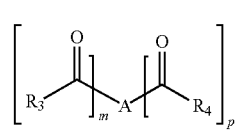

wherein A is a linear or branched unsubstituted $C_1$-$C_{20}$ alkylene or a linear or branched $C_1$-$C_{20}$ alkylene substituted by —C(O)OR$^1$, —C(O)O$^-$ or —OH, or A is a linear or branched unsubstituted $C_1$-$C_{20}$ alkylene interrupted by —O— or —NR$^2$— or a linear or branched $C_1$-$C_{20}$ alkylene interrupted by —O— or —NR$^2$ substituted by —C(O)OR$^1$, —C(O)O$^-$ or —OH;
wherein R$^1$ is hydrogen, unsubstituted linear or branched $C_1$-$C_{20}$ alkylene, linear or branched $C_1$-$C_{20}$ alkylene substituted by —C(O)OH, —C(O)O$^-$ or —OH; and
R$^2$ is hydrogen or linear or branched $C_1$-$C_{20}$ alkylene substituted by —C(O)OH or —OH;
m and p are 1 or 2; and
R$^3$ and R$^4$ are independently —OH, halogen, —OR$^5$, —OC(O), which —OC(O) may be bound to A to form an anhydride, or R$^3$ is oxygen and R$^4$ is a bond to the oxygen of R$^3$, and
R$^5$ is a $C_1$-$C_4$ alkyl or a substituted or unsubstituted phenyl.
4. The oral care composition according to claim 3, wherein A is a linear or branched unsubstituted $C_1$-$C_{10}$ or a linear or branched $C_1$-$C_{10}$ alkylene substituted by —C(O)OR$^1$, —C(O)O$^-$ or —OH, or A is a linear or branched unsubstituted $C_2$-$C_{10}$ alkylene interrupted by —$NR^2$— or a linear or branched $C_2$-$C_{10}$ alkylene interrupted by —$NR^2$— substituted by —$C(O)OR^1$, —$C(O)O^-$ or —OH; and $R^2$ is hydrogen or linear or branched C—C alkylene substituted by —C(O)OH or —OH.

5. The oral care composition according to claim 4, wherein A is a linear or branched unsubstituted $C_1$-$C_8$ alkylene or a linear or branched $C_1$-$C_8$ alkylene substituted by —$C(O)OR^1$, —$C(O)O^-$ and —OH, or A is a linear or branched $C_1$-$C_8$ interrupted by —$NR_2$—, and $R^2$ is $C_2$-$C_8$ alkylene substituted by —C(O)OH.

6. The oral care composition according to claim 1, wherein the polycarboxylic acid are selected from the group consisting of malonic acid, succinic acid, glutaric acid, adipic acid, pimelic acid, suberic acid, sebacic acid, azelaic acid, citric acid, diglycolic acid, 1,2,3-propanetricarboxylic acid, 1,1,3,3-propanetetracarboxylic acid, 1,1,2,2-ethane tetracarboxylic acid, 1,2,3,4-butanetetracarboxylic acid, 1,2,2,3 propanetetracarboxylic acid, 1,3,3,5 pentanetetracarboxylic acid, ethylenediaminetetraacetic dianhydride, malic acid, tartronic acid, isocitric acid, tartaric acid, mucic acid, gluconic acid, ethylenediamine tetraacetic acid, ethyleneglycolbis-tetraacetic acid, diglycolic acid, ethylenediamine tetrapropionic acid, iminodiacetic acid, 1,2-propylenediaminetetraacetic acid, Nmethyl, -ethyl, -propyl and -butyl iminodiacetic acid, 1,3-propylenediaminetetraacetic acid, N-hydroxyethylethylenediaminetriacetic acid, triethylenetetraminehexaacetic acid and diethylenetriaminepentaacetic acid.

7. The oral care composition according to claim 1, wherein the formed polymer is:

a polyesteramide of xylitol, arginine and succinic acid;

a polyesteramide of xylitol, arginine and ethylenediaminetetraacetic acid or dianhydride thereof; or a polyesteramide of xylitol, arginine and citric acid.

8. The oral care composition according to claim 1, wherein the formed polymer is a polyesteramide of xylitol, arginine and succinic acid.

9. The oral care composition according to claim 1, wherein the arginine makes up from about 3 to about 90 or about 95 wt. % of the total weight of the formed polymer.

10. The oral care composition according to claim 1, wherein the formed polymer has a Mw ranging from about Mw from about 500 to about 1,000,000.

11. The oral care composition according to claim 1, comprising at least one ingredient selected from the group consisting of surfactants, desensitizing agents, chelating agents, whitening agents, tartar control agents, antibacterial agents, abrasives including silica, binders and thickening agents, detergents, adhesion agents, foam modulators, pH modifying agents, mouth-feel agents, sweeteners, flavoring agents, colorants, preservatives and combinations thereof.

12. The oral care composition according to claim 11, wherein the ingredient is an antibacterial agent selected from the group consisting of triclosan, chlorhexidine or its salts. peroxides, phenols or their salts, domiphen bromide (phenododecinium bromide), bromochlorophene, stannous fluoride, Zn salts, chlorophylls, Cu salts, Cu gluconate, Cu chlorophyll, sodium lauryl sulfate, quarternary monoammonium salts pyridinium salts polysine, homopolymers of arginine, salts or complexes of arginine, stannous fluoride, thymol, menthol, methyl salicylate, eucalyptol and combinations thereof.

13. The oral care composition according to claim 12, wherein the antibacterial agent is selected from the group consisting of quarternary monoammonium salts pyridinium salts polylysine, triclosan, chlorhexidine and its salts and combinations thereof.

14. The oral care composition according to claim 1, wherein the formed polymer makes up about 0.01 to about 95 wt. % of the oral care composition.

15. The oral care composition according to claim 1, wherein the composition is a product selected from the group consisting of orally dissolvable films, whitening strips, mouthwashes, tooth pastes, dentifrices, oral lozenges, chewing gums and dental flosses.

\* \* \* \* \*